United States Patent [19]
Kohler et al.

[11] Patent Number: 5,523,208
[45] Date of Patent: Jun. 4, 1996

[54] METHOD TO DISCOVER GENETIC CODING REGIONS FOR COMPLEMENTARY INTERACTING PROTEINS BY SCANNING DNA SEQUENCE DATA BANKS

[75] Inventors: Heinz Kohler, Lexington, Ky.; J. Edwin Blalock, Mountain Brook, Ala.

[73] Assignee: The Board of Trustees of The University of Kentucky, Lexington, Ky.

[21] Appl. No.: 351,187

[22] Filed: Nov. 30, 1994

[51] Int. Cl.$^6$ .............. C12Q 1/68; C12P 21/06; G01N 33/00
[52] U.S. Cl. .............. 435/6; 435/7.1; 435/69.1; 435/91.5; 536/23.1; 436/86; 436/89; 436/94; 935/77
[58] Field of Search .............. 435/6, 91.5, 69.1, 435/7.1; 436/94, 86, 89; 935/77, 78

[56] References Cited

U.S. PATENT DOCUMENTS

| | | | |
|---|---|---|---|
| 4,675,283 | 1/1987 | Roninson | 435/6 |
| 4,820,630 | 4/1989 | Taub | 435/5 |
| 4,863,857 | 9/1989 | Blalock et al. | 435/68 |
| 4,921,952 | 5/1990 | Longmire et al. | 536/27 |
| 4,925,785 | 5/1990 | Wang et al. | 435/6 |
| 4,963,477 | 10/1990 | Tchen | 435/6 |
| 5,077,195 | 12/1991 | Blalock et al. | 435/6 |
| 5,081,584 | 1/1992 | Ominchinski | 364/497 |
| 5,190,856 | 3/1993 | Borresen | 435/6 |
| 5,208,144 | 5/1993 | Smith et al. | 435/6 |
| 5,242,794 | 9/1993 | Whiteley et al. | 435/6 |

FOREIGN PATENT DOCUMENTS

0411503A1  2/1991  European Pat. Off. .

OTHER PUBLICATIONS

Blalock, Trends in Biotechnology (1990) 8: 140–144.
Kaiser et al., Science, Jan. 20, 1984, vol. 223, No. 4633, Amphiphilic Secondary Structure: Design of Peptide Hormones, pp. 249–255.
Kyte et al., Journal of Molecular Biology, vol. 157, No. 1, May 5, 1982, A Simple Method for Displaying the Hydropathic Character of a Protein, pp. 105–132.
Burks et al., Journal of Cellular Biochemistry, Suppl. 9B, p. 153, 1985.
Itoh, K. et al., Gene, vol. 140, pp. 295–296, 1994.
Clark, A. et al., Journal of Bacteriology, vol. 175, No. 23, pp. 7673–7682, 1993.
Stuckle, E. et al., Nucleic Acids Research, vol. 18, No. 22, pp. 6641–6647, 1990.
Han, S. et al., Biochemistry, vol. 30, pp. 9678–9780, 1991.
Service, R. F. Science, vol. 263, 18 Mar. 1994, pp. 1559–1560.
Fichant, G. et al., Journal of Molecular Biology, vol. 220, pp. 659–671, 1991.

*Primary Examiner*—W. Gary Jones
*Assistant Examiner*—Carla Myers
*Attorney, Agent, or Firm*—Lowe, Price, LeBlanc & Becker

[57] ABSTRACT

A method for scanning nucleotide or DNA sequence data banks to identify genetic regions or genes coding for biologically interacting proteins.

13 Claims, 5 Drawing Sheets

METHOD TO DISCOVER GENETIC CODING REGIONS FOR COMPLEMENTARY INTERACTING PROTEINS BY SCANNING DNA SEQUENCE DATA BANKS

TECHNICAL FIELD

The present invention relates to a method for scanning nucleotide or DNA sequence data banks to identify genetic regions or genes coding for biologically interacting proteins.

BACKGROUND

Gene sequence and DNA sequence data bases are known. For example see "GenBank as a research tool—a computer based database for use in DNA sequencing (conference abstract)". Burks et al., J. Cell. Biochem. (Suppl.9B, 153) 1985. This publication discloses that Genbank, the national nucleotide sequence database, is a computer-based data bank of all published DNA and RNA sequences. The database is available on-line on tape and in hardcopy book form. As of September, 1984, the database contained close to 3.5 million nucleotides in over 4,000 entries. In addition to being a convenient reference for researchers interested in individual sequences, the database has been and is being designed to anticipate strategies that scan over many entries in search of similar features. Algorithms and software to accomplish these searches have been developed. Sequence comparison algorithms (used for identifying local homology, consensus sequences and hairpin structures), prediction of protein coding regions, and correlation of primary sequence data with both secondary and tertiary structure and functional roles in the cell are discussed.

U.S. Pat. No. 4,675,283 to Roninson discloses a method for detecting and isolating DNA sequences commonly held by different DNA preparations or repeated or amplified within a complex genome. When two different DNA preparations are hybridized to each other using the methodology of Roninson, DNA fragments of identical electrophoretic mobility and having homologous sequences can be detected.

U.S. Pat. No. 4,820,630 to Taub discloses a method of prenatal diagnosis of sickle cell anemia using a polymorphic HpaI site not located in the beta-globin gene itself, but rather in an adjacent sequence. This method of analysis is indirect and suitable only in those cases where the parents at risk can be shown to have the appropriate linked polymorphism prior to amniocentesis. Column 4, lines 1–6 indicates that the invention of Taub is applicable to genetic disorders for which the locus of the lesion, and either the normal or mutated sequence about the lesion, are known or isolatable. In one embodiment of the method of Taub, a first labeled probe, complementary to a 5' region of a site of interest, and a second labeled probe, complementary to a 3' region of the site of interest are utilized. If the site of interest constitutes a recognition/restriction site for an enzyme, digestion of the sampled DNA with that enzyme in hybridization of the restriction fragments to the labeled probes will separate the two labels and thus hinder their interaction to produce a signal.

U.S. Pat. No. 5,242,794 to Whiteley et al. discloses a method for diagnosis of genetic abnormalities or other genetic conditions which can be readily automated. The method is used to determine the presence or absence of a target sequence in a sample of denatured nucleic acid and entails hybridizing the sample with a probe complementary to a diagnostic portion of the target sequence, and with a probe complementary to a nucleotide sequence contiguous with the diagnostic portion under conditions wherein the diagnostic probe remains bound substantially only to the sample nucleic acid containing the target sequence. This patent relates to the detection of specific sequences of nucleotides in a variety of nucleic acid samples, and more particularly to those which contain a sequence characterized by a difference in a single base pair from a standard sequence.

U.S. Pat. No. 4,963,477 to Tchen issued Oct. 16, 1990. This patent is related to kit for detecting the presence of a nucleic acid sequence, such as a gene or a gene fragment, in a composition or a specimen suspected to contain that gene. The kit comprises a probe containing a nucleic acid complementary with the nucleic acid sequence or gene which is sought to be detected.

U.S. Pat. No. 4,925,785 to Wang et al. is directed to a method for carrying out a nucleic acid hybridization test to detect a target nucleic acid sequence. The method uses a single-stranded nucleic acid sequence capable of hybridizing to the target nucleic acid sequence and contacting a denatured target nucleic acid sequence with the single-stranded nucleic acid sequence to detect complexes between the target nucleic acid sequence and the first single-stranded nucleic acid sequence which is bonded to a polymer.

U.S. Pat. No. 5,208,144 to Smith et al. is directed to a method for the detection of human DNA which contains the gene encoding a low density lipoprotein receptor. The method involves three steps of isolating DNA that contains the gene encoding the low density lipoprotein receptor, contacting the DNA with DNA encoding gp330 for a time under conditions sufficient for hybridization to occur, and detecting the hybridization of the DNA with the gene encoding the gp330 DNA, wherein the presence of hybridization indicates the presence of DNA which contains the gene encoding the low density lipoprotein receptor.

U.S. Pat. No. 4,863,857 to Blalock et al. discloses polypeptides complementary to peptides or proteins having an amino acid sequence or nucleotide coding sequence at least partially known. This patent allows for a determination of the structure of polypeptides having particular structural and biological activities and affinities. The patent does not disclose a step of data base scanning to identify genes of unknown function.

U.S. Pat. No. 5,077,195 to Blalock et al. relates to polypeptides complementary to peptides or proteins having an amino acid sequence or nucleotide coding sequence at least partially known. This patent allows for the production of polypeptides which are complementary to known proteinaceous hormones. The polypeptides are capable of binding to the hormones and can be utilized to render the complementary hormone inactive. The patent does not disclose a step of data base scanning to identify genes of unknown function.

The Biotechnology News, dated Apr. 8, 1994, discloses that hereditary, non-polyposis colorectal cancer genes can be detected by scanning the Human Genome Sciences (HGS) data base for human genes similar to a known bacterial gene containing a similar sequence to the non-polyposis colorectal cancer gene.

Science, Volume 263, Mar. 18, 1994, pages 1559–1560, discloses the use of MutL bacterial probes containing the non-polyposis colon cancer gene of mice to isolate the gene in humans. The human DNA data base of Human Genome Sciences was scanned and the human gene associated with the colon cancer was located.

"Identifying potential tRNA genes in genomic DNA sequences", Fichant et al., (J. Mol. Biol. (ENGLAND) Aug. 5, 1991, 220 (3) pp. 659–71) discloses an algorithm that automatically and reproducibly identifies potential tRNA genes in genomic DNA sequences, and present a general strategy for testing the sensitivity of such algorithms. This algorithm is useful for the flagging and characterization of long genomic sequences that have not been experimentally analyzed for identification of functional regions, and for the scanning of nucleotide sequence databases for errors in the sequences and the functional assignments associated with them.

"Genetic and molecular analyses of the C-terminal region of the recE gene from the rac prophage of *Escherichia coli* K-12 reveal the recT gene". Clark et al., J. Bacteriol (UNITED STATES) December 1993, 175 (23) p. 7673–82A. A computer-performed scan of the bacteriophage nucleotide sequence data base of GenBank revealed substantial similarity between most of recE and a 2.5-kb portion of the b2 region of lambda. This suggests an evolutionary relationship of lambda and Rac prophages.

"Identification of an active gene by using large-scale cDNA sequencing". Itoh et al. Gene (NETHERLANDS) Mar. 25, 1994, 140 (2) p 295–6. A 3'-directed partial cDNA clone that matches exactly a genomic sequence in GenBank was isolated while collecting transcribed sequences from adult lung by a random approach. This is a report of active gene identification on genomic sequence without the aid of Northern hybridization.

"Characterization of the DNF15S2 locus on human chromosome 3: identification of a gene coding for four kringle domains with homology to hepatocyte growth factor". Han et al., Biochemistry (UNITED STATES) Oct. 8, 1991, 30 (40) p. 9768–80, discloses that the DNA sequence of the gene and cDNA and its translated amino acid sequence were compared against GenBank and NBRF databases. Sequences homologous to DNF15S1 and DNF15S2, human DNF15S2 lung mRNA, and rat acyl-peptide hydrolase were identified in exon 17 to the 3' end of the characterized sequence for the gene. From the results, it was apparent that the gene coding for human HGF-like protein is located at the DNF15S2 locus on human chromosome 3 (3p21). The gene for acyl-peptide hydrolase is 444 bp downstream of the gene coding for HGF-like protein, but on the complementary strand. The DNF15S2 locus has been proposed to code for one or more tumor suppressor genes since this locus is deleted in DNA from small cell lung carcinoma, other lung cancers, renal cell carcinoma, and von Hippel-Lindau syndrome.

"Statistical analysis of nucleotide sequences—DNA sequence, RNA sequence database scanning". Stueckle et al., Nucleic Acids Res. (18, 22, 6641–47) 1990. In order to scan nucleic acid databases for potentially relevant but as yet unknown signals, an improved statistical model for pattern analysis of nucleic acid sequences was developed by modifying previous methods based on Markov chains. The importance of selecting the appropriate parameters in order for the method to function is demonstrated. The method allows the simultaneous analysis of several short sequences with unequal base frequencies and Markov order k not equal to 0 as is usually the case in databases. As a test of these modifications, it was demonstrated that in 797 *Escherichia coli* sequences (total length 1.2 million bases), stored in the GenBank database, there was a bias against palindromic hexamers which correspond to known restriction enzyme recognition sites. Correct choice of Markov order k and threshold value alpha was essential for obtaining correct results. For oligonucleotides of length (L) greater than 4 the value of k should be 2. For values of L less than or equal to 4, k should be L-2.

The prior work in this field has failed to provide a simple, accurate method for determining the function of unknown genes.

The present method provides a means of scanning data banks consisting of cloned genetic material, including but not limited to DNA, RNA, mRNA, tRNA and nucleotide fragments, to identify the function of genetic material of unknown function. The method is simple, accurate and rapid.

DISCLOSURE OF THE INVENTION

Thus, it is an object of the present invention to provide a method for scanning DNA sequence data banks to identify and discover genetic regions coding for complementary/ biologically interacting proteins.

The invention can be used to scan DNA banks consisting of cloned DNA fragments of unidentified genes. The present invention makes it possible to search random DNA sequence data in a rational and disease specific manner and allows for the detection of known and unknown protein affinities which may have yet undiscovered biological functions.

The method, when used on DNA fragments of unknown coding potential will produce a list of gene fragments which code for proteins having the potential to form complexes or multimeric configurations with the unknown protein. Often these proteins are part of an enzymatic cascade.

Thus, the invention provides for a processing method for determining the function of a nucleotide sequence or amino acid sequence of unknown function with inverse hydropathy to at least a portion of an amino acid sequence with a known function in a genetic data base, comprising the steps of:

(a) obtaining a nucleotide sequence of unknown function;

(b) translating the nucleotide sequence of unknown function to an amino acid sequence;

(c) translating the genetic data base of nucleotide sequences of known function to amino acid sequences;

(d) determining hydropathy of sequence of step (b)

(e) determining hydropathy of sequences of step (c)

(f) comparing result of step (d) with result of step (e) for regions of inverse hydropathy;

(g) determining function of nucleotide sequence of unknown function based upon inverse hydropathy with the nucleotide sequence of known biologically interacting function.

In an alternative embodiment, the invention provides a method for determining the function of an amino acid sequence of a polypeptide with inverse hydropathy to at least a portion of an amino acid sequence of known function in a genetic data base comprising the steps of:

(a) obtaining a nucleotide sequence of known function;

(b) translating nucleotide sequence of known function to an amino acid sequence;

(c) translating genetic data base of nucleotide sequences of unknown function to amino acid sequences;

(d) determining hydropathy of sequence of step (b)

(e) determining hydropathy of sequence of step (c)

(f) comparing result of step (d) with result of step (e) for regions of inverse hydropathy;

(g) determining the function of the nucleotide sequence of unknown function based upon inverse hydropathy with the nucleotide sequence of known biologically interacting function.

In still another embodiment is provided a method for determining the function of a nucleotide sequence or gene sequence of unknown function with inverse hydropathy to at least a portion of a nucleotide or gene sequence with a known function in a genetic data base, comprising the steps of:

(a) obtaining a nucleotide sequence of unknown function;

(b) determining the hydropathy of the second position of each triplet codon of the nucleotide sequence of unknown function;

(c) determining the hydropathy of the second position of each triplet codon of a nucleotide sequence in genetic data base of nucleotide sequences of known function;

(d) comparing result of step (b) with result of step (c) for regions of inverse hydropathy;

(e) determining function of nucleotide sequence of unknown function based upon inverse hydropathy with the nucleotide sequence of known biologically interacting function.

Conversely, a method is provided for determining the function of a nucleotide sequence or gene sequence of known function with inverse hydropathy to at least a portion of a nucleotide or gene sequence with a unknown function in a genetic data base, comprising the steps of:

(a) obtaining a nucleotide sequence of known function;

(b) determining the hydropathy of the second position of each triplet codon of the nucleotide sequence of known function;

(c) determining the hydropathy of the second position of each triplet codon of a nucleotide sequence in genetic data base of nucleotide sequences of unknown function;

(d) comparing result of step (b) with result of step (c) for regions of inverse hydropathy;

(e) determining function of nucleotide sequence of unknown function based upon inverse hydropathy with the nucleotide sequence of known biologically interacting function.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

The method of the present invention scans data banks consisting of cloned genetic material, including but not limited to DNA, RNA, mRNA, tRNA and nucleotide fragments to identify the function of genetic material of unknown function.

The present invention builds upon the earlier discovery of Blalock et al., U.S. Pat. Nos. 4,863,857 and 5,077,195 (incorporated herein by reference in their entireties). Earlier work showed the non-coding strand of a gene contains information useful to design peptides which bind to proteins or peptides encoded by the coding DNA strand. This phenomenon is derived from the chemical relationship of the genetic code and the hydropathic character of encoded amino acids.

Blalock et al. earlier found that the non-coding strand of a gene contains information useful to design peptides which bind to proteins or peptides encoded by the coding DNA strand. The present invention provides a simple method for scanning DNA banks consisting of cloned DNA fragments of unidentified genes to identify the function of the gene. The invention makes it possible to search random DNA sequence data in a rational and disease specific manner and allows for the detection of previously unknown utility of DNA, which was previously unavailable.

The present invention extends the earlier work of Blalock et al. to a new and unrelated application, that of identifying genetic regions or genes which code for proteins which interact biologically (chemically) through data base scanning.

The method of the present invention can be used to scan gene data banks to detect known and unknown protein affinities which may have yet undiscovered biologic functions, which can be correlated to gene segments with known functions.

The method used on DNA fragments of unknown coding potential will produce a list of gene fragments which code for proteins having the potential to form complexes or multimeric configurations. Often these proteins are part of an enzymatic cascade, a signal pathway or of receptor-ligand families.

Probes can be made consisting of either peptides or specific antibodies which can be used as inhibitors or as tags of biologically active molecules found to be involved in a given disease. The DNA sequence known to code for a specific protein can be used as probe to identify the other, yet unknown genes which are part of a biologically interacting protein chain. By this method of complementary gene "bootstrapping", new interacting protein cascades can be discovered.

In accordance with the method of the present invention, it is now possible to identify the function of DNA of unknown function isolated from a tissue or culture sample and sequenced, by scanning DNA sequence data banks. This newly identified DNA may code for biologically and medically important proteins.

In addition, the current interest in the human genome research project has led to the establishment of commercial institutions which clone and sequence randomly isolated fragments from the human genome. Millennium and Human Genome Sciences are examples of two commercial enterprises which are producing human DNA sequence data.

One commercial application the method of the present invention for determining the function of genes of unknown function would be the use by companies or institutions involved in the identification of specific genetic diseases. The present invention makes it possible to search random DNA sequence data in a rational and disease specific manner to determine its function.

The interactions of biologically significant molecules are a basis of intercellular and interorgan communications. The particular biologically significant communicating molecules are, for example, peptide hormones and peptide-containing cellular receptors. A basis and rational explanation for their communicative interactions have long been sought.

A fundamental relationship has been found to exist between antiparallel base-pairing strands of nucleic acids. In one aspect, this relationship may give rise to pairs of peptides where each member of a particular pair has an affinity for the other member. The basic relationship is demonstrated in Table 1 where the various codons and their complementary (i.e. base pairing) codons are presented. The codons of a coding strand, (e.g. that strand containing the coding information describing an amino acid sequence) are represented as being read from left to right (the 5' to 3' direction). The codons of the complementary (i.e. noncoding) antiparallel base-paired strand are also read from in the 5' to 3' direction. Noncoding and coding nucleic acid strands pair when lying in an antiparallel direction (e.g. coding strand from left to right being 5' to 3' and noncoding strand from left to right being 3' to 5') so that the paired codons are viewed lying in an opposite observable direction (e.g. left to right vs. right to left) when read in the 5' to 3' direction. The codons given in Table 1 have been grouped suggestively by hydropathy as defined by Kyte et al. This specific grouping is used for illustrative purposes only and should not be viewed as restrictive of the scope of the present invention. As can be seen in Table 1, the complementary codons pairing with codons for the hydrophobic (high hydropathy) amino acids exhibit a tendency to code for hydrophilic (low hydropathy) amino acids. The reciprocal situation is shown with codons of the hydrophilic amino acids. For the slightly hydrophilic amino acids (slightly negative hydropathy), similar amino acids are coded for by the complementary codons. This relationship has great biological significance as described hereinafter.

TABLE 1

Amino Acids Whose Codons are Complementary to Those of the:

| Coding Strand | | Noncoding Strand | |
|---|---|---|---|
| Codon | Amino Acid | Codon | Amino Acid |

(1) Hydrophobic Amino Acids

TABLE 1-continued

Amino Acids Whose Codons are Complementary to Those of the:

| Coding Strand | | Noncoding Strand | |
|---|---|---|---|
| Codon | Amino Acid | Codon | Amino Acid |
| AUU | Isoleucine | AAU | Asparagine |
| AUC | Isoleucine | GAU | Aspartic acid |
| AUA | Isoleucine | UAU | Tyrosine |
| GUU | Valine | AAC | Asparagine |
| GUC | Valine | GAC | Aspartic acid |
| GUG | Valine | CAC | Histidine |
| GUA | Valine | UAC | Tyrosine |
| CUU | Leucine | CAA | Glutamine |
| CUG | Leucine | CAG | Glutamine |
| UUU | Phenylalanine | AAA | Lysine |
| UUC | Phenylalanine | GAA | Glutamic acid |
| UGU | Cysteine | ACA | Threonine |
| UGC | Cysteine | GCA | Alanine |
| AUG | Methionine | CAU | Histidine |
| GCG | Alanine | CGC | Arginine |
| GCU | Alanine | AGC | Serine |
| GCC | Alanine | GCC | Glycine |
| GCA | Alanine | UGC | Cysteine |
| (2) Hydrophilic Amino Acids | | | |
| CGU | Arginine | CGU | Alanine |
| CGU | Arginine | ACG | Threonine |
| CGA | Arginine | ACG | Threonine |
| AGA | Arginine | UCU | Serine |
| CGG | Arginine | CCG | Proline |
| AGG | Arginine | CCU | Proline |
| AAG | Lysine | CUU | Leucine |
| AAA | Lysine | UUU | Phenylalanine |
| AAU | Asparagine | AUU | Isoleucine |
| AAC | Asparagine | GUU | Valine |
| GAU | Aspartic acid | AUU | Isoleucine |
| GAC | Aspartic acid | GUC | Valine |
| CAA | Glutamine | UUG | Leucine |
| CAG | Glutamine | CUG | Leucine |
| GAG | Glutamic acid | UUG | Leucine |
| GAA | Glutamic acid | UUC | Phenylalanine |
| CAC | Histidine | GUG | Valine |
| CAU | Histidine | AUG | Methionine |
| (3) Slightly Hydrophilic Amino Acid | | | |
| GGU | Glycine | ACC | Threonine |
| GGA | Glycine | UCC | Serine |
| GGG | Glycine | CCC | Proline |
| GGC | Glycine | GCC | Alanine |
| ACC | Threonine | GGU | Glycine |
| ACU | Threonine | CGU | Serine |
| ACG | Threonine | CGU | Arginine |
| ACA | Threonine | UGU | Cysteine |
| UGG | Tryptophan | CCA | Proline |
| UCC | Serine | GGA | Glycine |
| AGU | Serine | ACU | Threonine |
| UCG | Serine | CGA | Arginine |
| UCU | Serine | AGA | Arginine |
| AGC | Serine | GCU | Alanine |
| UAU | Tyrosine | AUA | Isoleucine |
| UAC | Tyrosine | GUA | Valine |
| CCC | Proline | GGG | Glycine |
| CCA | Proline | UCC | Tryptophan |
| CCU | Proline | AGG | Arginine |
| CCG | Proline | CGG | Arginine |

The paired codons (nucleotide triplets) in Table 1 result from comparing hypothetical coding nucleic acid strands (RNA in this ase) and non-coding nucleic acid strands (RNA paired in an antiparallel direction). Both strands were then read in the 5' to 3' direction and in the same reading frame to obtain the original codons and their complementary (base-paired) codons.

Of the possible 20 complementary codons for the hydrophobic amino acid-coding codons, only two (GCA and UCG) code for hydrophobic amino acids. Of the possible 18 complementary codons for the hydrophilic amino acid-coding codons, 13 coded for hydrophobic amino acids and 5 coded for slightly hydrophilic amino acids.

Of the possible 20 complementary codons for the slightly hydrophobic amino acids, 5 coded for strongly hydrophilic amino acids and 5 coded for strongly hydrophobic amino acids, the net comparative effect being little change in hydropathic character.

Table 2 lists the coded amino acids and their respective complementarily coded amino acids of Table 1 and includes their hydropathic scores (Kyte et al, 1982).

TABLE 2

HYDROPATHIC SCORES OF AMINO ACIDS AND THEIR COMPLEMENTS AS DESCRIBED IN TABLE 1

| AMINO ACIDS | SCORE | COMPLE-MENTS | SCORES | AVERAGE SCORE |
|---|---|---|---|---|
| ILE | +4.5 | ASN | −3.5 | |
| | | ASP | −3.5 | |
| | | TYR | −1.3 | −2.8 |
| VAL | +4.2 | ASN | −3.5 | |
| | | ASP | −3.5 | |
| | | HIS | −3.2 | |
| | | TYR | −1.3 | −2.9 |
| LEU | +3.7 | LYS | −3.9 | |
| | | GLU | −3.5 | |
| | | GLN | −3.5 | −3.6 |
| PHE | +2.7 | LYS | −3.9 | |
| | | GLU | −3.5 | −3.7 |
| CYS | +2.5 | THR | −0.7 | |
| | | ALA | +1.8 | +0.6 |
| MET | +1.9 | HIS | −3.2 | |
| ALA | +1.8 | ARG | −4.5 | |
| | | SER | −0.9 | |
| | | GLY | −0.4 | |
| | | CYS | +2.5 | −0.8 |
| ARG | −4.5 | ALA | +1.8 | |
| | | THR | −0.7 | |
| | | SER | −0.9 | |
| | | PRO | −1.6 | −0.5 |
| LYS | −3.9 | LEU | +3.7 | |
| | | PHE | +2.7 | +3.2 |
| ASN | −3.5 | ILE | +4.5 | |
| | | VAL | +4.2 | +4.4 |
| ASP | −3.5 | ILE | +4.5 | |
| | | VAL | +4.2 | +4.4 |
| GLN | −3.5 | LEU | +3.7 | +3.7 |
| GLU | −3.5 | LEU | +3.7 | |
| | | PHE | +2.7 | +3.2 |
| HIS | −3.2 | VAL | +4.2 | |
| | | MET | +1.9 | +3.1 |
| GLY | −0.4 | THR | −0.7 | |
| SER | −0.9 | | | |
| | | PRO | −1.6 | |
| | | ALA | +1.8 | −0.1 |
| THR | −0.7 | GLY | −0.4 | |
| | | SER | −0.9 | |
| | | ARG | −4.5 | |
| | | CYS | +2.5 | −0.8 |
| TYR | −0.9 | PRO | −1.6 | −1.6 |
| SER | −0.9 | GLY | −0.4 | |
| | | THR | −0.7 | |
| | | ARG | −4.5 | |
| | | ALA | +1.8 | −1.6 |
| TYR | −1.3 | ILE | +4.5 | |
| | | VAL | +4.2 | +4.4 |
| PRO | −1.6 | GLY | −0.4 | |
| | | TRY | −0.9 | |
| | | ARG | −4.5 | −2.5 |

As shown in Table 2 a general relationship exists as exemplified by sets of amino acids. For example, a first set of amino acids directed (i.e. coded for) by a first group of codons and a second set (complementarily coded) of amino acids are directed by a second group of codons complementary to the first group of codons. A relationship between the first set of amino acids and the second a set of amino acids is found which may be characterized as hydropathically inverse. In one instance, complementarily coded hydrophilic (low hydropathy) amino acids are directed by codons complementary to those coding for the hydrophobic (high hydropathy) amino acids. This relationship may be termed hydropathic complementary.

Figure 1:
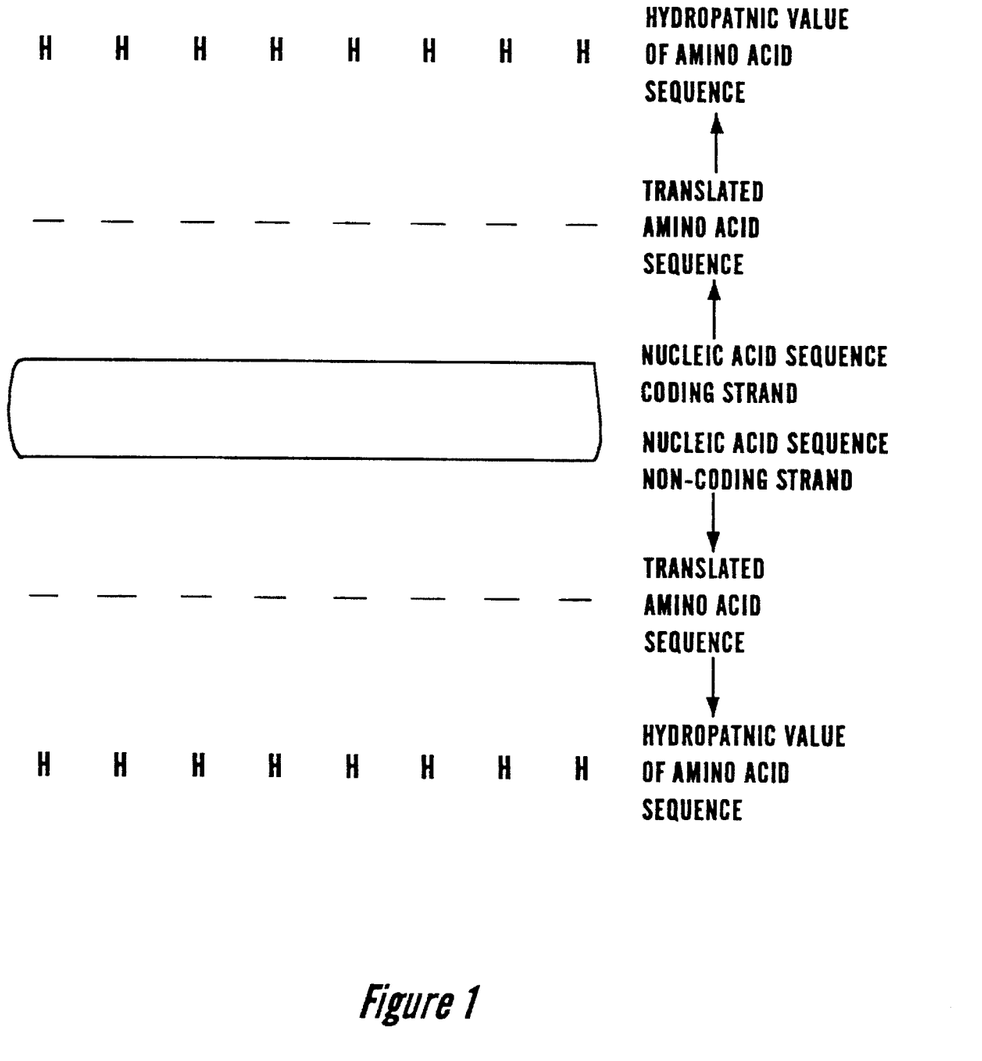
FIG. 1 shows the relationship between the hydropathy values assigned to the amino acid sequence of the coding strand of DNA to the hydropathy values assigned to the amino acid sequence of the non-coding strand of DNA. Hydropathy values are inverse.
Figure 2:
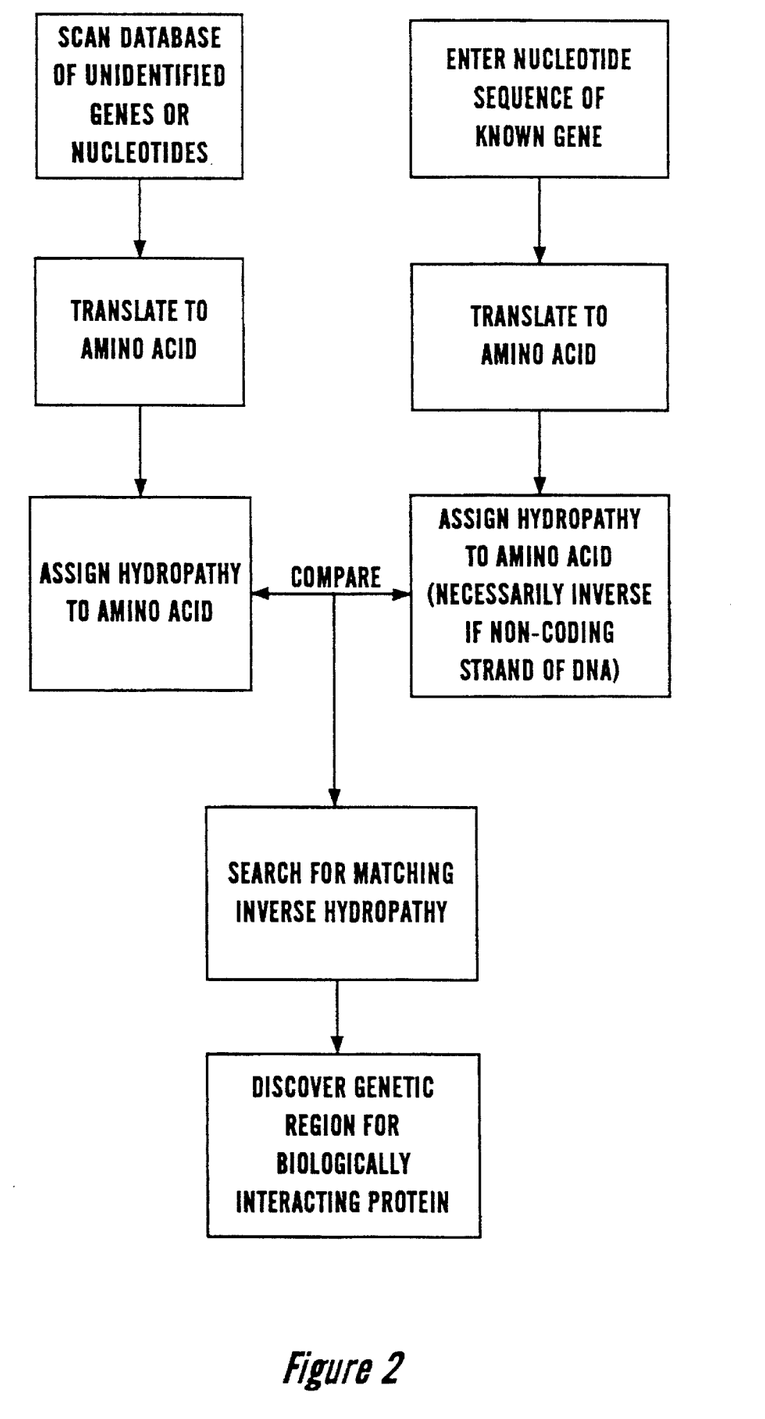
FIG. 2 shows a flow diagram of the method of the invention when scanning a data base of nucleotide sequences of unknown function with a reference nucleotide sequence of known function.
Figure 3:
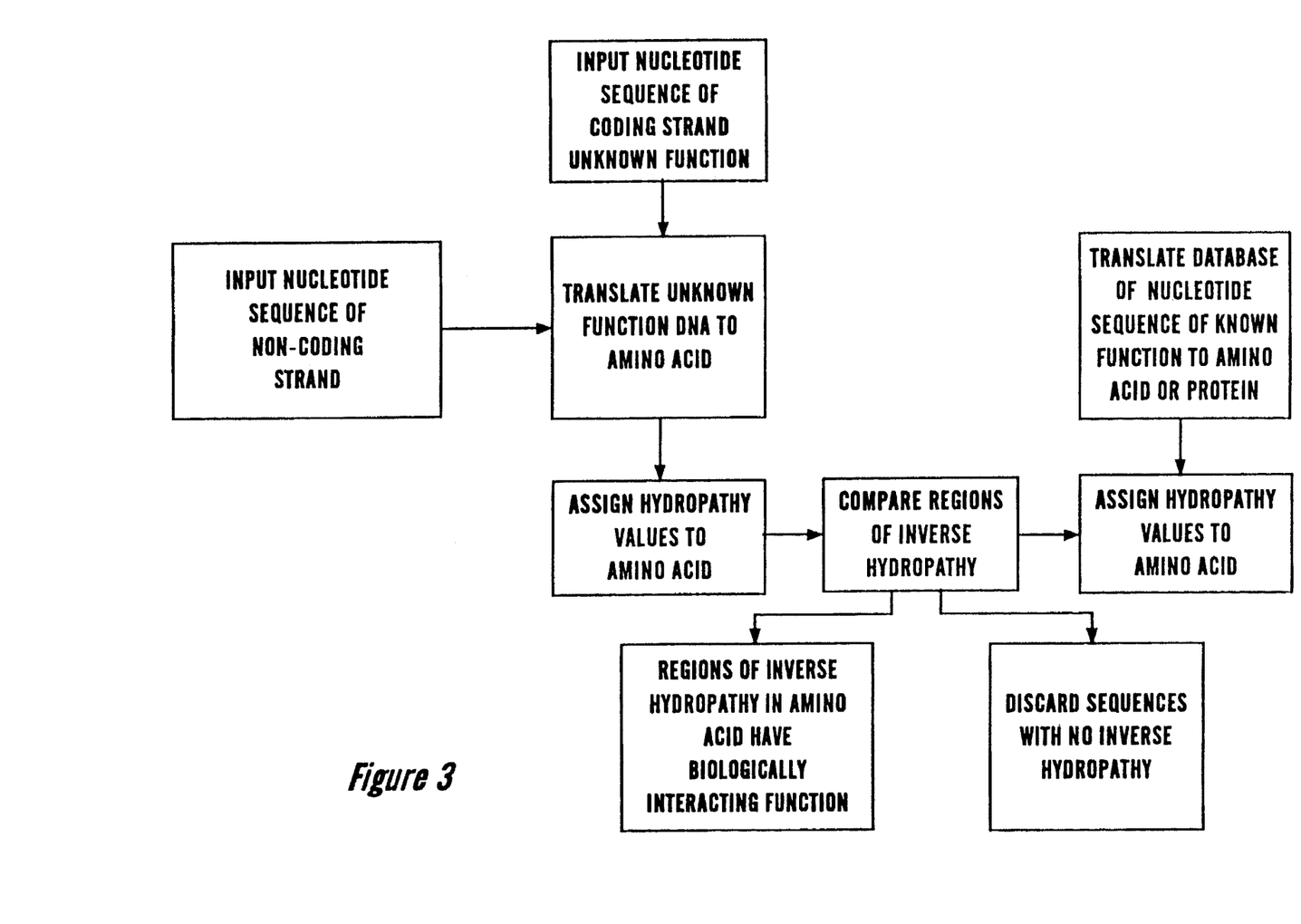
FIG. 3 shows a flow diagram of an alternative embodiment of the method of the invention when scanning a data base of nucleotide sequences of known function with a reference nucleotide sequence of unknown function.
Figure 4:
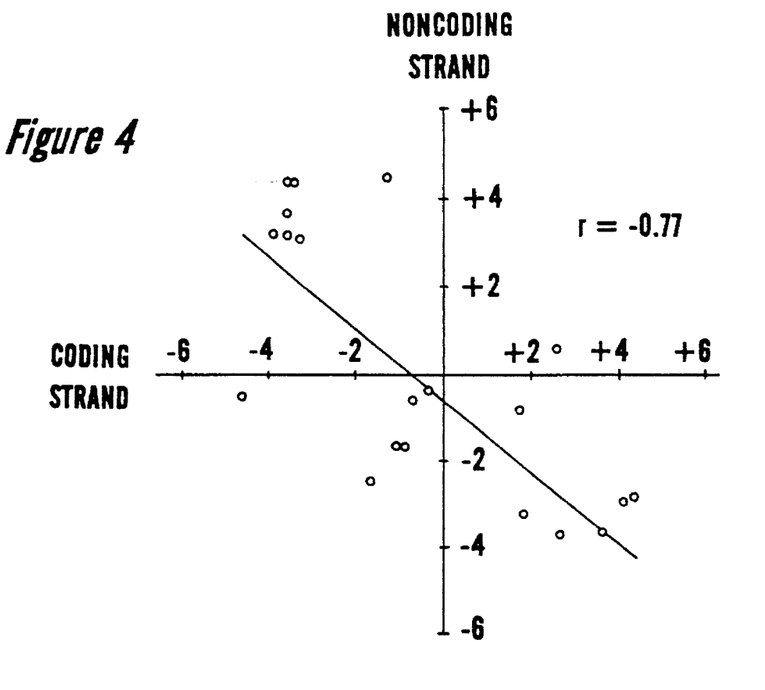
FIG. 4 shows a plot of data from Table 2 showing the hydropathic scores of the amino acids directed by codons of a coding nucleic acid strand versus the average hydropathic scores of the amino acids complementarily directed by the codons of the complementary noncoding strand.

FIG. 4 shows a plot of data from Table 2 showing the hydropathic scores of the amino acids directed by codons of a coding nucleic acid strand versus the average hydropathic scores of the amino acids complementarily directed by the codons of the complementary noncoding strand. A linear regression analysis of this data results in a correlation coefficient of −0.77. A similar pattern is observed when calculated by another hydropathic scoring system which has somewhat different values for tryptophan, tyrosine, glutamine and asparagine (data not shown, Hopp et al., Proc. Natl. Acad. Sci. (1981) Vol. 78 pp. 3824–3828). Thus the noncoding strand-directed amino acid hydropathic scores tend to be inversely related to the coding strand amino acid hydropathic scores and this relationship is not random and could be found with any scoring system reflecting amino acid properties reflecting hydrophobic and hydrophilic tendencies, alone or in combination with other physical properties of amino acids.

Interestingly, a similar relationship also arises when the complementary codons are read in the 3' to 5' direction. The coding relationships of complementary codons read in the 3' to 5' direction are shown in Table 3.

TABLE 3

Amino acids Whose Codons are Complementary to Those of:

| Coding Strand | | Noncoding Strand | |
|---|---|---|---|
| Codon | Amino Acid | Codon | Amino Acid |
| (1) Hydrophobic Amino Acids | | | |
| AUA | Isoleucine | UAU | Tyrosine |
| GUU | Valine | CAA | Glutamine |
| GUC | Valine | CAG | Glutamine |
| GUG | Valine | CAC | Histidine |
| GUA | Valine | CAU | Histidine |
| UUA | Leucine | AAU | Asparagine |
| UUG | Leucine | AAC | Asparagine |
| CUU | Leucine | GAA | Glutamic Acid |
| CUC | Leucine | GAG | Glutamic Acid |
| CUA | Leucine | GAU | Aspartic Acid |
| CUG | Leucine | GAC | Aspartic Acid |
| UUU | Phenylalanine | AAA | Lysine |
| UUC | Phenylalanine | AAG | Lysine |
| UGU | Cysteine | ACA | Threonine |
| UGC | Cysteine | ACG | Threonine |
| AUG | Methionine | UAC | Tyrosine |
| GCU | Alanine | CGA | Arginine |
| GCC | Alanine | CGG | Arginine |
| GCA | Alanine | CGU | Arginine |
| GCG | Alanine | CGC | Arginine |
| (2) Hydrophilic Amino Acids | | | |
| CGU | Arginine | GCA | Alanine |
| CGC | Arginine | GCG | Alanine |
| CGA | Arginine | GCU | Alanine |
| CGG | Arginine | GCC | Alanine |
| AGA | Arginine | UCU | Serine |
| AGG | Arginine | UCC | Serine |

TABLE 3-continued

Amino acids Whose Codons are Complementary to Those of:

| Coding Strand | | Noncoding Strand | |
|---|---|---|---|
| Codon | Amino Acid | Codon | Amino Acid |
| AAA | Lysine | UUU | Phenylalanine |
| AAG | Lysine | UUC | Phenylalanine |
| AAU | Asparagine | UUA | Leucine |
| AAC | Asparagine | UUG | Leucine |
| GAU | Aspartic Acid | CUA | Leucine |
| GAC | Aspartic Acid | CUG | Leucine |
| CAA | Glutamine | GUU | Valine |
| CAG | Glutamine | GUC | Valine |
| GAG | Glutamic Acid | CUC | Leucine |
| GAA | Glutamic Acid | CUU | Leucine |
| CAC | Histidine | GUG | Valine |
| CAU | Histidine | GUA | Valine |
| (3) Slightly Hydrophilic Amino Acids | | | |
| GGU | Glycine | CCA | Proline |
| GGC | Glycine | CCG | Proline |
| GGA | Glycine | CCU | Proline |
| GGG | Glycine | CCC | Proline |
| ACC | Threonine | UGG | Tryptophan |
| ACG | Threonine | UCG | Cysteine |
| ACA | Threonine | UGU | Cysteine |
| UGG | Tryptophan | ACC | Threonine |
| UCU | Serine | AGA | Arginine |
| UCC | Serine | AGG | Arginine |
| UCA | Serine | AGU | Serine |
| UCG | Serine | AGC | Serine |
| AGU | Serine | UCA | Serine |
| AGC | Serine | UCG | Serine |
| UAU | Tyrosine −1.3 | AUA | Isoleucine |
| UAC | Tyrosine | AUG | Methionine |
| CCU | Proline −1.6 | GGA | Glycine |
| CCC | Proline | GGG | Glycine |
| CCA | Proline | GGU | Glycine |
| CCG | Proline | GGC | Glycine |

As shown in Table 3, of the 20 possible condons complementary, to, the codons for hydrophobic amino acids, when read in the 3' to 5' direction, none coded for hydrophobic amino acids, 16 coded for hydrophilic amino acids and 4 (UAU, ACA, ACG and UAC) coded for slightly hydrophilic amino acids.

Of the 18 possible codons complementary to the codons for the strongly hydrophilic amino acids, when read in the 3' to 5' direction, none coded for strongly hydrophilic amino acids, 16 for hydrophobic amino acids and two (UCU and UCC) for slightly hydrophilic amino acids.

Table 4 lists the hydropathic scores of amino acids and their complements (i.e. amino acids complementarily coded or coded by respective complementary codons) described in Table 3.

TABLE 4

HYDROPATHIC SCORES OF AMINO ACIDS AND THEIR COMPLEMENTS AS DESCRIBED IN TABLE 3

| AMINO ACID | SCORE | COMPLEMENTS | SCORES |
|---|---|---|---|
| ILE | +4.5 | TYR | −1.3 |
| VAL | +4.2 | GLN | −3.5 |
| | | HIS | −3.2 |
| LEU | +3.7 | ASN | −3.5 |
| | | GLU | −3.5 |
| | | ASP | −3.5 |
| PHE | +2.7 | LYS | −3.9 |
| CYS | +2.5 | THR | −0.7 |
| MET | +1.9 | | −1.3 |
| ALA | +1.8 | ARG | −4.5 |
| ARG | −4.5 | ALA | +1.8 |
| | | SER | −0.9 |
| LYS | −3.9 | PHE | +2.7 |
| ASN | −3.5 | LEU | +3.7 |
| ASP | −3.5 | LEU | +3.7 |
| GLN | −3.5 | VAL | +4.2 |
| GLU | −3.5 | LEU | +3.7 |
| HIS | −3.2 | VAL | +4.2 |
| GLY | −0.4 | PRO | −1.6 |
| THR | −0.7 | TRY | −0.9 |
| | | CYS | +2.5 |
| TRY | −0.9 | THR | −0.7 |
| SER | −0.9 | ARG | −4.5 |
| | | SER | −0.9 |
| TYR | −1.3 | ILE | +4.5 |
| | | MET | +1.9 |
| PRO | −1.6 | GLY | −0.4 |

Of the possible complementary codons to the codons coding for slightly hydrophilic amino acids, when read in the 3' to 5' direction, 14 code for slightly hydrophilic amino acids, 2 (ACA and ACG) code for strongly hydrophilic amino acids and 4 (UCG, UGU, AUA and AUG) code for hydrophobic amino acids. The net effect here being little change in the average hydropathic character of the noncoding strand amino acids.

Figure 5:
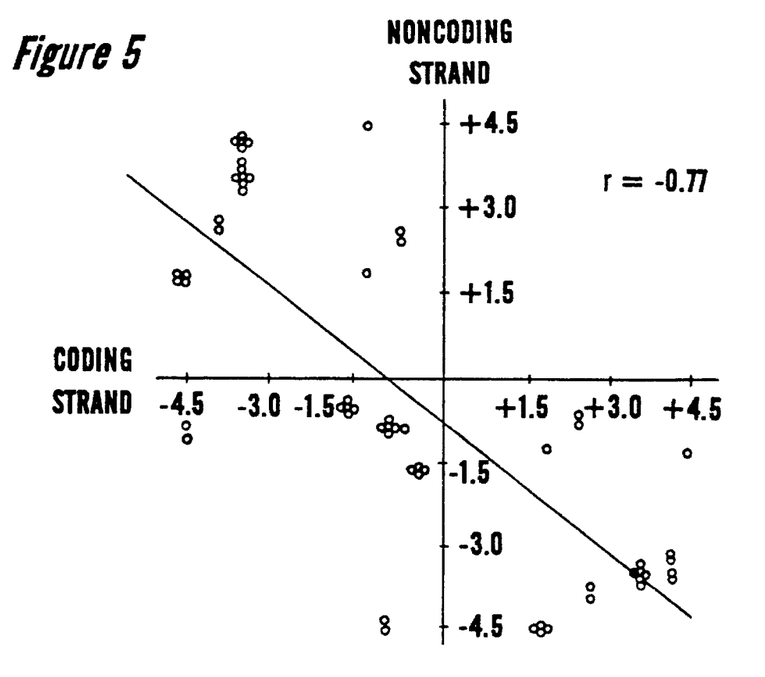
FIG. 5 shows a plot of the hydropathic scores of the coding strand amino acids versus the hydropathic scores of the noncoding strand amino acids.

FIG. 5 shows a plot of the hydropathic scores of the coding strand amino acids versus the hydropathic scores of the noncoding strand amino acids. A linear regression analysis of this data results in a correlation coefficient of −0.77. Thus, as was the case for the 5' to 3' direction, in the 3' to 5' direction, the noncoding strand amino acid hydropathic scores are inversely related to those of the coding strand and this relationship is not random.

These relationships of information contained in the genetic code demonstrate a hydropathic complementary of amino acids. Codons, when read in the 5' to 3' direction, for hydrophilic and hydrophobic amino acids were generally complemented by codons for hydrophobic and hydrophilic amino acids, respectively. The average tendency of codons for "uncharged" (slightly hydrophilic) amino acids was to be complemented by codons for "uncharged" amino acids.

As demonstrated by these observations an almost identical pattern results when the complementary nucleotide codon is read in the 3' to 5' rather than the 5' to 3' direction. Since, regardless of the reading direction, the second nucleotide of the complementary codon never changes, this second nucleotide of the triplet codon is the principal determinant for the hydropathic complementary of amino acids which are specified by complementary codons. This seems to largely result from the fact that the preponderance (6 out of 7) of hydrophilic amino acids have adenine as their second nucleotide codon while the complementary nucleotide uridine, is the second nucleotide of the triplet codon for most (5 of 7) hydrophobic amino acids. One of the 2 exceptions to the above in the hydrophobic group (alanine) does not seriously vitiate the above generality as it has a second base, cytosine, while the second base for the single exception in the hydrophilic group (arginine) has a second base, guanine. Hence, there is a virtually perfect interchange of hydrophobic and hydrophilic amino acids whether the complementary codon is read in the 5' to 3' or 3' to 5' direction. Of the six uncharged (slightly hydrophilic) amino acids with the exception of tyrosine, the second base of the respective codons is either a G or C. Hence, the codons for this group will usually result in a similar type of amino acid regardless of the direction in which the complementary codon is read.

Table 5 lists amino acids whose codons contain a particular second (middle) base.

TABLE 5

Amino Acids having a Particular Second Base in their Codons

| SECOND BASE OF RNA CODON | AMINO ACIDS |
|---|---|
| U | ILE |
|   | VAL |
|   | LEU |
|   | PHE |
|   | MET |
| A | LYS |
|   | ASN |
|   | ASP |
|   | GLN |
|   | GLU |
|   | HIS |
|   | TYR |
| G | CYS |
|   | ARG |
|   | GLY |
|   | TRY |
|   | SER |
| C | THR |
|   | SER |
|   | PRO |
|   | ALA |

The group of amino acids (U group) directed by a uridine second base have a complementarily coded group of amino acids (A group) coded by an adenine second base, and vice versa. The cytosine and guanine directed groups (C group and G group respectively) have the same relationship.

Table 6 lists the hydropathic scores of amino acids directed by codons having a particular second base and, for convenience separately shows corresponding scores for the complementarily coded amino acids (complement). Again, the hydropathically complementary relationship is illustrated.

TABLE 6

HYDROPATHIC SCORES OF AMINO ACIDS AND THEIR COMPLEMENTS BASED ON GROUPINGS SHOWN IN TABLE 5

| Second Base Group | | | Average Hydropathic Scores | |
|---|---|---|---|---|
| | | | Coded | Complement |
| U | ILE | +4.5 | | |
|   | VAL | +4.2 | | |
|   | LEU | +3.7 | | |
|   | PHE | +2.7 | | |
|   | MET | +1.9 | +3.4 | -3.2 |
| A | LYS | -3.9 | | |
|   | ASN | -3.5 | | |
|   | ASP | -3.5 | | |
|   | GLN | -3.5 | | |
|   | GLU | -3.5 | | |
|   | HIS | -3.2 | | |
|   | TYR | -1.3 | -3.2 | +3.4 |

TABLE 6-continued

HYDROPATHIC SCORES OF AMINO ACIDS AND THEIR COMPLEMENTS BASED ON GROUPINGS SHOWN IN TABLE 5

| Second Base Group | | | Average Hydropathic Scores | |
|---|---|---|---|---|
| | | | Coded | Complement |
| G | CYS | -2.5 | | |
|   | ARG | -4.5 | | |
|   | GLY | -0.4 | | |
|   | TRY | -0.9 | | |
|   | SER | -0.9 | -0.8 | -0.4 |
| C | THR | -0.7 | | |
|   | SER | -0.9 | | |
|   | PRO | -1.6 | | |
|   | ALA | +1.8 | -0.4 | -0.8 |

Figure 6:
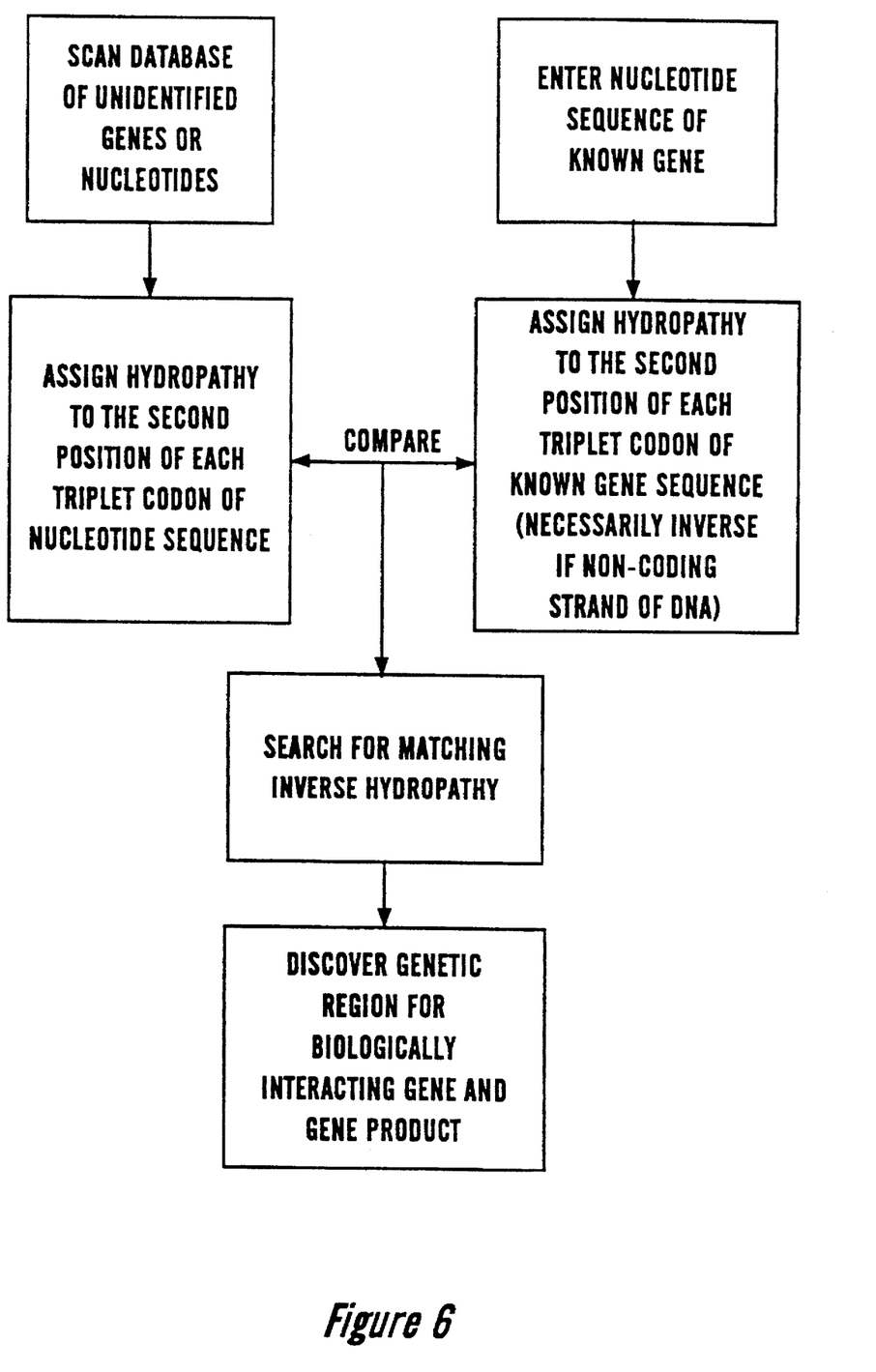
FIG. 6 shows a flow diagram of an alternative embodiment of the method of the invention when scanning a data base of nucleotide sequences of known function with a reference nucleotide sequence of unknown function where a hydropathy value is assigned to the second position of each triplet codon of the sequence.

From Tables 2, 4 and 6 it can be seen that peptides and their complements are related by a general inversion of hydropathic nature on an amino acid by amino acid basis, when the sequences are aligned in a parallel or anti-parallel manner depending on the method of generation. Preferred embodiments of the present invention, as demonstrated by utilization of the specific codon relationships shown in Table 1 and Table 3 are special cases of a more generally defined method to generate complementary peptides. See method outlined in FIG. 6.

When nucleic acid sequences are not known, the general methods based on second base complementary or hydropathic inversion may be used to locate homologs of the specifically preferred complementary peptides. For example, when an amino acid sequence but not the particular codons for all or a portion of a protein or peptide is known, a complementary peptide may be designed based upon the general relationships shown in Table 6. For an the amino acid in the original protein or peptide sequence having a second codon base of uridine (U group amino acid), an amino acid for the A group is substituted and vice versa. For an amino acid in the protein or peptide sequence having a second codon base of cytosine (C group), an amino acid from the guanine (G group) is substituted and vice versa. After these substitutions the sequence of amino acids thus obtained will be complementary to respective portions of the original peptide or protein.

Tables 1, 3 and 6 can be used in a general manner when the nucleic acid sequences are not known. In such cases, for an amino acid in the original peptide or protein sequence, an amino acid is substituted from the corresponding set of non-coding strand amino acids.

After these substitutions, the sequence of amino acids thus obtained will be complementary to the respective portions of the original peptide or protein. As a further extension of the principles of the present invention, the specific directionality of the complementary amino acid sequence may not be critical. As is clear to one skilled in the art upon study of the entire description presented herein, the juxtaposition of amino acids in construction of complementary polypeptide may be directionally oriented in either of two ways. Relative to the amino acid sequence directing positioning of amino acids having particular hydropathic character, the amino terminal and carboxy terminal directions are interchangeable, both constructions giving rise to complementary polypeptides. In simpler form, for one example, if the amino terminal end of a particular amino acid sequence contains a valine (second codon base=U), then a complementary amino acid sequence would contain, at the amino terminal end or the carboxy terminal end, an amino acid having a second codon base A (LYS, ASN, ASP, GLN, GLU, HIS, or TYR), using the general method based on Table 6.

For purposes of clarification and consistency, the following terms are defined as to their general meaning herein.

The term antiparallel, referring to nucleic acid pairings, indicates a directionality as to the paired nucleic acids. The original nucleic acid may be in a 5' to 3' direction where the 5' and 3' refer to positions on the sugar moieties involved in nucleotide coupling. The second nucleic acid strand base-paired or complementary to the original nucleic acid strand lies in a 3' to 5' direction when linearly aligned with the original strand having a 5' to 3 directionality.

The coding nucleic acid contains the sequence of nucleotide triplets (codons) specifying a sequence of amino acids when read in a 5' to 3' direction. The noncoding (complementary) nucleic acid (or nucleic acid strand) is complementary to the coding nucleic acid (or nucleic acid strand), the strands lying or base-pairing in an antiparallel direction.

The term hydropathic complementarity, referring to the hydropathic scores (a relative measure of hydrophilicity and hydrophobicity) of amino acids indicates a low hydropathy corresponding to a high hydropathy and vice versa. In referring to structures comprising amino acids, they are generally referred to as peptides, polypeptides or proteins, this order designating an increase in size between, for example, dipeptides, oligopeptides, and proteins containing many hundred of amino acids.

The term complementary, as used herein has a meaning based upon its context of usage. For example, complementary bases or nucleotides are those characteristically forming hydrogen bonds (G-C and A-T or A-U), complementary codons nucleic acids or strands thereof are hydrogen bonded polynucleotide components of a double nucleic acid strand such of that in the classically defined double helix for example complementary amino acids usually having hydropathic complementary are those directed by members of a pair of complementary codons.

Complementary peptides or polypeptides and their related original peptide or protein are a pair of peptides directed by complementary nucleotide or amino acid sequences, and characteristically have a binding affinity between members of a pair. Polypeptides complementary to a peptide or at least a portion of a protein, for example, have a binding affinity for the peptide or protein portion. While peptide binding affinities are incompletely understood, they may, in part at least, be explained by the concept of amphiphilic secondary structure described by Kaiser et al (Science (1984) Vol. 223 pp. 249–255).

The complementary polypeptide whose amino acid sequence is thus determined may be obtained by diverse means such as, for example, chemical synthesis, derivation from a protein or larger polypeptide containing said amino acid sequence, or, when the second nucleic acid is DNA, inserting the second nucleotide sequence into a plasmid to form a recombinant DNA plasmid vector and transforming a unicellular organism therewith to produce a transformant unicellular organism biosynthesizing said complementary polypeptide.

The genetic code may have arisen during evolution as a result of the chemical similarity of anticodonic bases and their respective amino acids. Perhaps this similarity resulted in the patterns observed herein. A functional and evolutionary advantage to this phenomenon may reside in the fact that the second base of codons for hydropathically similar amino acids is the same. Perhaps, prior to the advent of the directionality of nucleic acid reading, an amino acid from the same hydropathic group would be present and thus the resulting peptides or proteins would be grossly similar in conformation, whether nucleic acids were read 5' to 3' or 3' to 5'.

Thus, polypeptides of unknown function with inverse hydropathy to at least a portion of an original peptide or protein having known amino acid sequence, or nucleotide coding sequence have binding affinity to the original peptide or protein may be located in a sequence data bank. If the amino acid sequence of at least a portion (for example four to five amino acids) of an original peptide or protein is known, information of that sequence may be used in several ways to locate a complementary polypeptide in a nucleotide sequence data bank.

The ability to systematically scan a data base of genetic material using a polypeptide of unknown function that will interact with or bind to known proteins, based on structural considerations of the known protein, constitutes a scientific breakthrough of major proportions in the field of peptide and/or chemistry and medicinal pharmacology. The ability to rapidly and simply identify the functions of gene sequences of unknown function is also of utmost importance.

One aspect the present invention is related to the identification of the function of unknown polypeptides capable of specifically interacting with selected target peptide structures of a known amino acid sequence and known function.

In accordance with the present invention a computer program may aid in the identification of interaction sites between unknown and known proteins to determine the function of unknown proteins. The program compares the hydropathic profiles of the two interacting proteins and reports sites demonstrating an exact pattern of inverted hydropathy.

This can be accomplished with a structured computer program written in C language which scans and compares the hydropathic profiles (based on the Kyte and Doolittle scoring of individual residues, (Kyte, J., and Doolittle, R. F. (1982) J. Mol. Biol., Vol. 157, pp. 105–132)) of the two interacting proteins, and reports sites (hits) where the average difference in hydropathy is greater than or equal to the user-defined limit. Considerable data suggest that these regions of inverted hydropathy (whose amino acid lengths can be controlled by opening or closing the window size that is scanned) are potential docking or interactive sites between these two proteins. (Blalock, J. E. (1990) Trends Biol. Tech., Vol. 8, pp. 140–144; Jarpe, M. A., and Blalock, J. E. (1994) in Peptides: Design, Synthesis, and Biological Activity (Basava, C., and Anantharamaiah, G. M., Eds.), in press, Springer-Verlag, New York, N.Y.)

A computer program, named SITESEARCH (Fassina, G. (1989) Eur. Pat. Appl. EP 411,503; Fasisna, G., Verdoliva, A., Cassani, G., and Melli, M. (1994) Growth Factors, in press; Palla, E., Bensi, G., Solito, E., Tornese-Buonamassa, D., Fassina, G., Raugei, G., Spano, F., Galeotti, C., Mora, M., Domenighini, M., Rossini, M., Gallo, E., Carinci, V., Bugnoli, M., Bertini, F., Parente, L., and Melli, M. (1993) J. Biol. Chem., Vol. 268, pp. 13486–13492), is able to compare the hydropathic profiles of the protein and receptor sequences under investigation, and to determine the sequence stretches characterized by the highest level of hydropathic complementarity. The program uses the Kyte and Doolittle algorithm for calculating the hydropathic profile of each segment of predefined length L (generally between 5 and 11 residues) in the two chains under examination. For each segment pair of length L, the program determines also the hydropathic complementarity score θ, which is an indicator of the degree of complementarity. The lower score, the higher the hydropathic complementarity. In other words, the programs scan the receptor and protein sequences simultaneously to find the highest complementary sites.

Computer-Assisted Identification of Hydropathically Complementary Sequences

Given the amino acid sequences of the two interacting polypeptides $P_a$ and $P_b$, the corresponding moving average hydropathy values, $a_i$ and $b_i$, are calculated in accordance with the formulae $$a_i=\Sigma h_k(P_a)/r$$

$$b_i=\Sigma h_k(P_b)/r,$$

with $$S<i<n-S,$$

where k is (i−S) to (i+S), r is an odd number defined as the run length (r<n), and S is equal to (r−1)/2 for each residue i of the first and second sequence. The hydropathic index h for each amino acid is obtained from the Kyte and Doolittle scale (16) as follows:

Subsequently, the hydropathic complementarity score, $\theta_i$, defined in accordance with the formula:

$$\theta_i=\Sigma\sqrt{(a_i+b_i)^2/L}$$

where L is the predefined searching length (3, 5, 7, 9, or 11 residues), is counted for all the possible fragments of length L contained in $P_a$ and $P_b$. Scores above 2.5 indicate poor complementarity and characterize a large number of sequence pairs.

X-ray crystallographic studies and computer modeling of structures (Davies, D. R., and Padlan, E. A. (1990) *Annu. Rev. Biochem.*, Vol. 59, pp. 439–73; Novotny, J., Handschumacher, M., and Haber, E. (1986) *J. Mol. Biol.*, Vol. 189, pp. 715–721; Martin, A. C. R., Cheetham, J. C., and Rees, A. R. (1989) *Proc. Natl. Acad. Sci. USA*, Vol. 86, pp. 9286–9272; Chothia, C., and Lesk, A. M. (1987) *J. Mol. Biol.*, Vol. 196, pp. 901–917; Chothia, C., Lesk, A. M., Tramontano, A., Levitt, M., Smith-Gill, S. J., Air, G., Sheriff, S., Alzari, P. M., and Poljak, R. J. (1989), *Nature*, Vol. 342, pp. 877–883) can be extremely useful in determining which residues of conformational proteins are surface accessible and can thus be potential contributors to biologically interacting sites such as an idiotope or anti-idiotope structure in a protein. This knowledge can be combined with the complementary hydropathy program to effectively filter out the noise (residues that match but are buried in the folded protein) and obtain which residues are involved in biological contact and interaction. If regions of a nucleotide are surface accessible in the folded proteins, they are considered putative binding or docking sites and can be confirmed through laboratory testing.

EXAMPLE

For example, an inverse hydropathy computer program may be used to determine the function of an unknown nucleotide or DNA sequence, Sequence C7. The sequence of C7 is entered into the a computer system. A computer program translates the unknown gene to protein and assigns hydropathy values. Then the genetic data base to be searched is selected. If the genetic data based has gene sequences or sequences other than amino acid sequences stored, the gene or other sequence must first be converted to its amino acid sequence or protein. Hydropathy values are assigned to the known protein sequence.

The hydropathy values of the unknown amino acid sequence or protein are compared with those hydropathy values of known amino acid sequences or proteins and regions of inverse hydropathy are indicated and displayed in a display screen compatible with the computer means for comparing hydropathy values. The function of unknown C7 gene is determined based upon inverse hydropathy with known genes in the genetic sequence data base.

When hydropathic regions of C7 are compared to the hydropathic regions of known proteins in GenBank, sites of hydropathic complementarity (inverse hydropathy) in C7 that also have sequential homology with myelin basic protein (MBP) acetyl 1-9 were located. Thus the function of C7 was determined to be that of biologically interacting with MBP acetyl 1-9. (Zhou, S.-R., and Whitaker, J. N. (1992), *Clin. Immunol. Immuno-pathol.*, Vol. 63, pp. 74–83.)

This method of identifying genetic function of a nucleotide sequence is dependent on the determinant being somewhat linear as opposed to being composed entirely of discontinuous single residues which are brought within proximity of one another in the tertiary structure by folding. Complementarity determining regions (CDRs), generally the site of the idiotope or anti-idiotope, loop out to form continuous structures exposed on the surface of Ig and therefore are likely candidates for meeting this criteria.

The data indicates that the Ag-combining site (in the CDRs) of C7 bears an internal image of MBP acetyl 1-9 and that this structure comprises a portion of the antiidiotope expressed in another anti-MBP acetyl 1-9 Mab, F23C6 (29), further supporting the idea that C7 bears an internal image of MBP acetyl 1-9. C7 binds both the VH and the VL of F28C4 and F23C6 by immunoblotting the denatured chains after separation of SDS-PAGE. This indicates that the idiotopes are located in both chains and are composed of linear sequences. (Zhou, S.-R., and Whitaker, J. N. (1992), *Clin. Immunol. Immuno-pathol.*, Vol. 63, pp. 74–83.)

Such findings identify the residues comprising the MBP 1-9 internal image in C7 by four criteria: (1) identify hits of hydropathic complementarity between F28C4 and the CDRs of C7, (ii) identify hits of hydropathic complementarity between F23C6 and the CDRs of C7, (iii) identify hits of hydropathic complementarity between MBP 9-1 and the CDRs of C7, and (iv) identify sites of sequence homology between MBP acetyl 1-9 and the CDRs of C7. Sites in the CDRs of C7 where all four criteria overlap are expected to be representative of the MBP 1-9 internal image and comprise, at least in part, the anti-idiotope of C7. Upon analysis of the sequences, sites of inverted hydropathy were found in both VH CDR 3 and VL CDR 1 of C7 relative to Ab1.

A paradigm for generating and the characterizing of hybridomas used in this study is described in detail elsewhere. (Zhou, S.-R., and Whitaker, J. N. (1992), *Clin. Immunol. Immuno-pathol.*, Vol. 63, pp. 74–83; Zhou, S.-R. and Whitaker, J. N. (1990) *J. Immunol.*, Vol. 145, pp. 2554—2560.)

Analysis of hydropathic complementarity

Hydropathy scores assigned to amino acids are based on the Kyte and Doolittle scale which extends from most hydrophobic (+4.5) to most hydrophilic (−4.5) (Kyte, J., and Doolittle, R. F. (1982), *J. Mol. Biol.*, Vol 157, pp. 105–132). The sequences of variable regions are entered into the program and the heavy and light chains of F28C4 or F23C6 are compared to the sequences of C7. The sequences are compared in both orientations. Parameters can be modified to increase or decrease the stringency of what is considered a hit. For the F28C4:C7 and F23C6:C7 searches, the parameter settings are: (i) search a window site of five amino acids (hits are searched for in a window of five residues, sliding the window down the sequence one amino acid at a time), (ii) average chain complementarity set at 0.80 (this value represents the average of the differences in the hydropathic scores of aligned amino acids for the window size selected; the closer to 0 the better the complementarity), and (iii) the cutoff point for considering if two amino acids are opposite, set to 1.0 (the absolute value of the two aligned residues added together, this value is denoted the cutoff). For the MBP 9-1:C7 search, the window was reduced to three amino acids, while keeping the average chain complementarity and the cutoff the same as above.

The sequences of C7 were determined and then entered into the complementary hydropathy program and compared to F28C4 (36), F23C6 (35), and MBP 9-1 to identify which resides might be involved in the terminal image of MBP 1-9 and also other residues which might further contribute to the anti-idiotope of C7. Since the antigen inhibits the binding of C7, the internal image portion of the anti-idiotope is expected to reside in the CDRs of C7; therefore, only hits lying in or near the CDRs (as defined by Kabat et al., (Kabat, E. A., Wu, T. T., Perry, H. M., Gottesman, K. S., and Foeller, C. (1991) in Sequences of Proteins of Immunological Interest, 5th ed., U.S. Department of Health and Human Services, National Institutes of Health, Bethesda, Md.) of C7 were considered. The CDR 3, including part of framework (FR) 3, of C7 VH matched with all four proteins; complementarity with F28C4, F23C6, and PBM 9-1 and homology with MBP 1-9. The CDR 1 of C7 matched with three of the proteins, F28C4, F23C6, and MBP 1-9. Other hits with F28C4 or F23C6 were found in other CDRs, and while these might indicate anti-idiotope structures, they probably do not include the internal image structure because they do not match with MBP 1-9.

To confirm that the hits identified in C7 with F28C4, F23C6 and MBP 9-1 represent the MBP 1-9 internal image of C7, a short, six-amino-acid peptide having the C7 sequence homology matches with MBP 1-9 is synthesized. This synthetic peptide, denoted L1H3, has the sequence of $Ala_{25}Ser_{26}Gln_{27}$ from VL CDR 1, combined with the $Arg_{94}His_{95}Gly_{96}$ from VH FR 3/CDR 3. L1H3 inhibits the binding of F28C4 to MBP 1-9, although approximately 1000-fold more L1H3 peptide was required to reach 50% inhibition than with the MBP 1-9 peptide (2.6 nmol vs 4.3 pmol, respectively), suggesting that an epitope occurs on L1H3, which is antigenically similar to the epitope on MBP 1-9. L1H3 also partially inhibits C7 binding to F28C4. This inhibition is very similar to the inhibition seen with MBP 109 (40% inhibition at 154 nmol vs 49% inhibition at 85 nmol, respectively), suggesting that this site contains the MBP 1-9 internal image.

The complementary or inverse hydropathy program aids in the identification of the C7 residues comprising the MBP 1-9 internal image. This structure is found to be comprised of two short linear sequences from two different CDRs of C7. It is possible that this two regions can be juxtaposed in the native, folded Fab to create one longer contiguous structure which can then mimic the MBP 1-9 epitope.

Therefore, each hit should be tested (e.g., with peptide inhibition studies or site directed mutational analysis) to determine its contribution to contact. This approach of delineating interactive sites of proteins through the identification of complementary hydropathic cassettes has broad applications.

In sum, the present method provides a means of scanning data banks consisting of cloned genetic material, including but not limited to DNA, RNA, mRNA, tRNA and nucleotide fragments, to identify the function of genetic material of unknown function isolated from a sample. The genetic material whose function has been identified by this method can then be tested to confirm pharmaceutical and medicinal properties.

Thus, the purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A method for determining the biological interaction of a nucleotide sequence of unknown biological interaction with inverse hydropathy to at least a portion of an amino acid sequence with a known function and biological interaction in a genetic data base, comprising the steps of:
   (a) obtaining a nucleotide sequence of unknown biological interaction;
   (b) translating the nucleotide sequence of unknown interaction to an amino acid sequence;
   (c) translating the genetic data base of nucleotide sequences of known biological interaction to amino acid sequences;
   (d) determining hydropathy of sequence of step (b)
   (e) determining hydropathy of sequences of step (c)
   (f) comparing result of step (d) with result of step (e) for regions of inverse hydropathy;
   (g) determining biological interaction of said nucleotide sequence of unknown biological interaction based upon inverse hydropathy with the nucleotide sequence of known biological interaction.

2. A method for determining the biological interaction of an amino acid sequence of a polypeptide with inverse hydropathy to at least a portion of an amino acid sequence of known function and biological interaction in a genetic data base comprising the steps of:
   (a) obtaining a nucleotide sequence of known biological interaction;
   (b) translating nucleotide sequence of known biological interaction to an amino acid sequence;
   (c) translating genetic data base of nucleotide sequences of unknown biological interaction to amino acid sequences;
   (d) determining hydropathy of sequence of step (b)
   (e) determining hydropathy of sequence of step (c)
   (f) comparing result of step (d) with result of step (e) for regions of inverse hydropathy;
   (g) determining the biological interaction of said amino acid sequence of a polypeptide based upon inverse hydropathy with the amino acid sequence of step (b).

3. A method according to claim 1, wherein said nucleotide sequence of known biological interaction is DNA.

4. A method according to claim 1, wherein said nucleotide sequence of known biological interaction is mRNA.

5. A method according to claim 1 wherein the nucleotide sequence of unknown biological interaction is read in the 5' to 3' direction.

6. A method according to claim 1 wherein the nucleotide sequence of unknown biological interaction is read in the 3' to 5' direction.

7. A method according to claim 1 wherein the nucleotide sequence of known biological interaction is an amino acid coding nucleotide sequence.

8. A method according to claim 1 wherein the nucleotide sequence of known biological interaction is a non-coding strand of a double stranded DNA.

9. A method according to claim 1 wherein the nucleotide sequence of biologically interacting function encodes a protein involved in a biological interaction selected from the group consisting of enzymatic cascade, signal pathway and receptor-ligand biological interaction.

10. A method for determining the biological interaction of a nucleotide sequence of unknown biological interaction wherein said biological interaction is selected from the group consisting of enzymatic cascade, signal pathway and receptor-ligand biological interaction, with inverse hydropathy to at least a portion of a nucleotide sequence with a known function and biological interaction in a genetic data base, comprising the steps of:

(a) obtaining a nucleotide sequence of unknown biological interaction;

(b) determining the hydropathy of the second position of each triplet codon of the nucleotide sequence of unknown biological interaction;

(c) determining the hydropathy of the second position of each triplet codon of a nucleotide sequence in genetic data base of nucleotide sequences of known biological interaction;

(d) comparing result of step (b) with result of step (c) for regions of inverse hydropathy;

(e) determining biological interaction of nucleotide sequence of unknown biological interaction based upon inverse hydropathy with the nucleotide sequence of known biological interaction.

11. A method for determining the biological interaction of a nucleotide sequence of known function and biological interaction with inverse hydropathy to at least a portion of a nucleotide sequence with a unknown biological interaction in a genetic data base, comprising the steps of:

(a) obtaining a nucleotide sequence of known biological interaction;

(b) determining the hydropathy of the second position of each triplet codon of the nucleotide sequence of known biological interaction;

(c) determining the hydropathy of the second position of each triplet codon of a nucleotide sequence in genetic data base of nucleotide sequences of unknown biological interaction;

(d) comparing result of step (b) with result of step (c) for regions of inverse hydropathy;

(e) determining biological interaction of nucleotide sequence of unknown biological interaction based upon inverse hydropathy with the nucleotide sequence of known biological interaction.

12. The method of claim 1, further comprising the step of confirming the biological interaction of the nucleotide sequence of unknown biological interaction by testing the activity of the nucleotide sequence of unknown biological interaction and comparing test results with known activity of the nucleotide sequence of known biological interaction.

13. The method of claim 1, wherein said nucleotide sequence of unknown biological interaction is isolated from a sample and sequenced.

* * * * *